United States Patent [19]
Tarwater

[11] Patent Number: 5,213,746
[45] Date of Patent: May 25, 1993

[54] WAX CASTING PROCESS FOR PRODUCING A CASTING OF A BODY PART

[76] Inventor: Ross Tarwater, 1206 Richmond Ave., Chesapeake, Va. 23324

[21] Appl. No.: 716,272

[22] Filed: Jun. 17, 1991

[51] Int. Cl.⁵ .............................................. B29C 33/76
[52] U.S. Cl. ................................... 264/221; 264/222; 264/317
[58] Field of Search ............... 264/221, 222, 223, 317, 264/DIG. 30

[56] References Cited

U.S. PATENT DOCUMENTS

| | | | |
|---|---|---|---|
| 47,121 | 4/1865 | Mills | 264/221 |
| 803,004 | 1/1905 | Mayer | 264/222 |
| 996,783 | 7/1911 | Moreau | 264/222 |
| 1,020,679 | 3/1912 | Barrows et al. | 264/222 |
| 2,178,873 | 11/1939 | Feinbloom | 264/222 |
| 2,281,227 | 4/1942 | Brady | 264/222 |
| 2,473,723 | 6/1949 | Nelson | 264/222 |
| 3,612,147 | 10/1971 | Kaplan | 264/28 |
| 3,894,136 | 7/1975 | Waddill | 264/245 |
| 4,274,823 | 6/1981 | Stanciu | 264/328.19 |
| 4,735,754 | 4/1988 | Buckner | 264/221 |
| 4,842,243 | 6/1989 | Butler | 264/221 |

*Primary Examiner*—Richard L. Chiesa
*Assistant Examiner*—Robert B. Davis
*Attorney, Agent, or Firm*—Wallace J. Nelson

[57] ABSTRACT

A process for obtaining precision castings of body parts wherein the body part is first immersed in a ice and water slush, immediately removed therefrom and immersed in a melted paraffin wax-water container, immediately removed therefrom and the body part extracted from the resulting wax mold. At least the interior surface of the hollow wax mold is coated with a casting material and permitted to cure at room temperature. The cured casting is heated by immersion in the wax-water container or in a separate heated water container for a period of at least ten minutes to remove the wax mold and recover a casting of the body part. The removed wax molding material may be recycled and employed in subsequent castings and recover a casting of the body part.

7 Claims, 1 Drawing Sheet

WAX CASTING PROCESS FOR PRODUCING A CASTING OF A BODY PART

FIELD OF THE INVENTION

This invention relates broadly to a casting process and relates specifically to apparatus and process for utilizing a wax molding for casting replicas of body parts and the like.

BACKGROUND OF THE INVENTION

Cast replicas of body parts such as the hands, face, feet are frequently employed by artists and actors and may be also required in medical and legal applications. Cast face, and other body part moldings, are presently made by making a negative plaster cast of the body part, generally in multiple stages, which leaves seams that must be worked or refined after the mold is cast. This is a multi-step, time consuming, expensive and wasteful procedure since essentially none of the materials employed are suitable for re-use or recycling. In addition, professional or highly skilled labor is required to obtain the desired accurate castings by this prior art process. There is a definite need in the art for a simple, inexpensive, casting procedure that may be employed for making castings of body parts in a fraction of the time required by the prior art methods and wherein the materials utilized in the process are recoverable and recyclable.

Accordingly, it is an object of the present invention to provide a novel process of making castings of body parts, and the like, that is simple and inexpensive to perform.

An additional object of the present invention is a process for making castings of body parts, and the like, that may be performed in a fraction of the time required by prior art methods.

Another object of the present invention is a process of making castings of body parts that may be performed accurately with the use of semi-skilled labor.

A further object of the present invention is a casting process that employs recyclable materials in the producing the mold for the casting.

SUMMARY OF THE INVENTION

According to the present invention, the foregoing and additional objects are attained by providing a first container of ice and water and a second container having a quantity of water and a quantity of wax therein. The second container is heated to a temperature adequate to maintain the wax contained therein in a melted or liquid state. The body part to be cast is provided with a coating of glycerin, light oil or other suitable release agent and immersed momentarily into the ice water, immediately removed from the ice water and immersed in the melted wax-water container, immediately removed from the melted wax-water container, and while still warm, the body part is removed from the wax coating thereon to provide an accurate mold of the body part to be cast. After cooling to room temperature, the wax mold is coated or filled with a liquid or paste casting material and permitted to cure.

Suitable casting materials include casting resins, gypsum based products such as plaster of paris, Hydrocal, Hydrosone, and the like. After curing to a hardened state the cast and mold are immersed in a hot water bath for approximately ten minutes to melt the wax and recover the casting of the body part. This hot water bath may be the same wax-water container or a separate container of water only heated to essentially boiling point. The melted wax may be recovered and recycled for use in making subsequent casting molds.

BRIEF DESCRIPTION OF THE DRAWINGS

A more complete appreciation of the invention and many of the attendant advantages thereof will be more readily apparent as the same becomes better understood by reference to the following detailed description when considered in connection with the accompanying drawings wherein.

DETAILED DESCRIPTION

Figure 1:
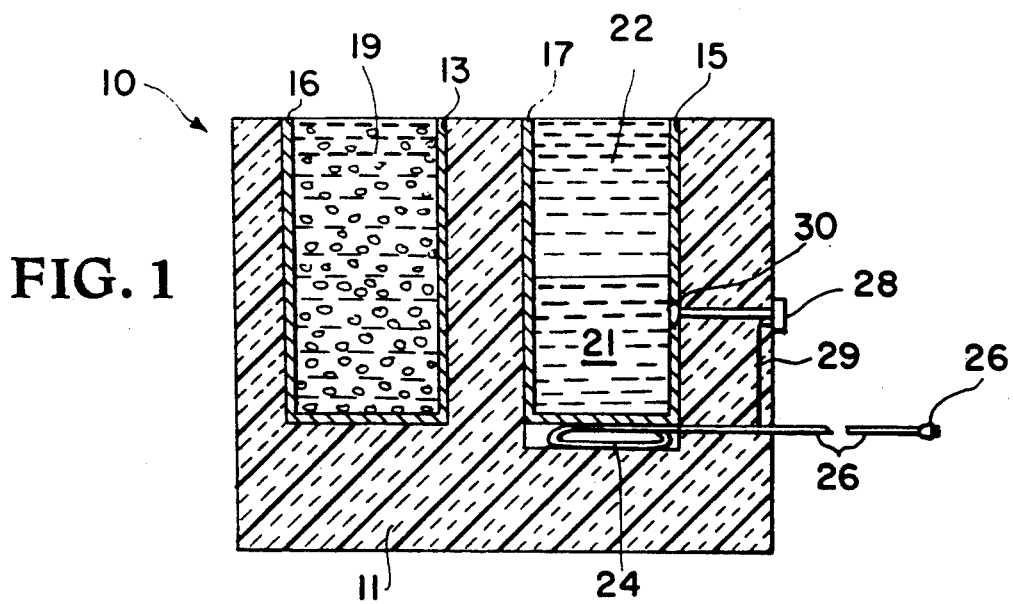
FIG. 1 is a sectional view of the insulated container housing and heating system employed in the mold casting process of the present invention.

Referring now to the drawings, and more particularly to FIG. 1, there is shown a housing for the components employed in making the wax mold for the casting process of the present invention and designated generally by reference numeral 10. Housing 10 is filled with a thermal insulating material 11 with a pair of cavities 13 and 15 provided therein for receiving a pair of containers, designated respectively by reference numerals 16, 17. Container 16 is provided with a quantity of ice-water slush 19 therein while Container 17 has a quantity of water 21 and a quantity of paraffin wax 22 therein. Containers 16 and 17 are preferably formed of stainless steel but may also be formed of aluminum, pyrex glass, or the like.

A suitable heating element or coil 24 is provided within container housing 10, supported by insulation material 11 and at the base of cavity 15. Heating coil 24 is in electrical connection with an electrical lead line 25 having a plug 26 thereon for electrical connection with a suitable electric power source, not shown. A thermostatic control switch 28 is secured to the exterior wall of housing 10 and is in electrical connection with lead line 25 through connection wire 29 and thermocouple 30. Thermostatic control switch 28 controls the input of electric power to electrical heating coil 24, in a conventional manner, and as will be further explained hereinafter. Thermocouple 30 is disposed within cavity 15 so as to be in contact with the exterior of container 17 disposed therein.

Figure 2:
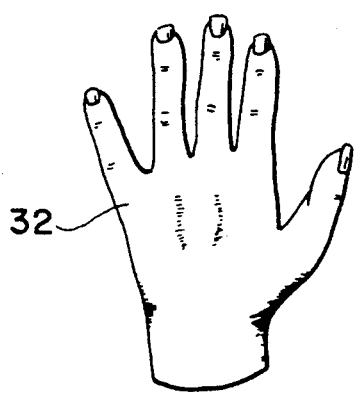
FIG. 2 is a view of a casting of a child's hand produced by the process of the present invention.

Referring now to FIG. 2 a casting of a single human hand (child's) prepared by the process of the present invention is illustrated and designated by reference numeral 32. This casting may be appropriate for medical, legal or memento purposes for growing children, aging parents, and the like.

Figure 3:
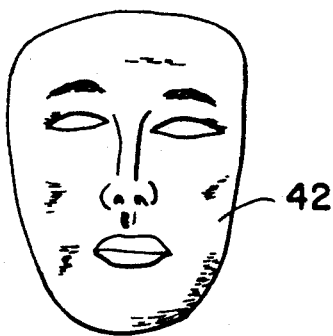
FIG. 3 is a view of a casting of a face produced by the process of the present invention.

FIG. 3 illustrates a casting of a human face prepared by the process of the present invention and designated by reference numeral 42. This casting may also be appropriate for medical and/or legal purposes, stage theatrics, children and adult memento preservation, and the like.

Figure 4:
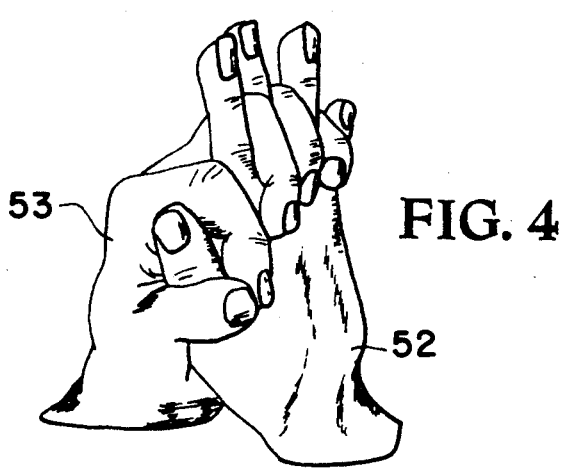
FIG. 4 is a view of a casting of joined hands of a couple produced by the present invention; and, FIG. 5 is a view of a casting of a pair of hands holding an object produced by the present invention.

FIG. 4 illustrates a casting of clasped hands of different individuals prepared by the process of the present invention and designated by reference numerals 52,53. This casting would be appropriate for making at weddings, anniversaries, mother and child, husband and wife, two children, or the like.

Figure 5:
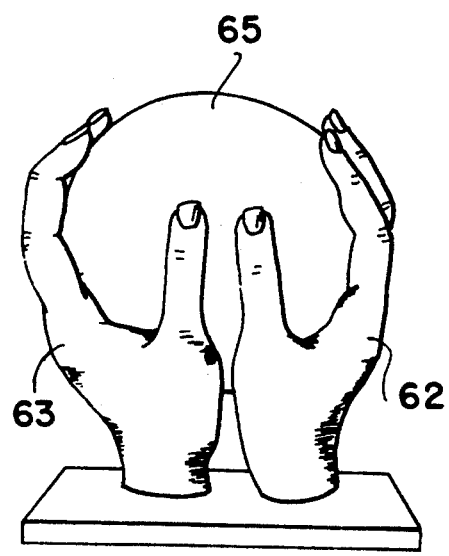

FIG. 5 illustrates a pair of hands 62,63 (which may belong to the same person or different individuals) holding an object 65 of significance for a specific occasion.

OPERATION

The operation of the invention is now believed apparent. Utilizing the apparatus shown in FIG. 1, any one of the castings shown in FIGS. 2-4 may be produced. Container 16 is filled with an ice and water slush and the bottom half of container 17 is filled with water and a top layer of paraffin wax added to essentially fill the container. Electrical plug 26 is connected to a suitable source of electrical current and thermostat switch 28 set at the desired temperature within the temperature range of 100°-120° F. A conventional light may be provided on thermostat control switch 28 to burn until container 17 reaches the desired temperature as detected by thermocouple 30.

The body part to be cast is coated with a suitable release agent and immersed in the ice water slurry 19 in container 16. Immediately thereafter, the body part is removed from the ice water slurry and immersed in the melted wax and water in container 17 and immediately removed therefrom. The body part is then extracted from the wax layer formed thereon to recover a hollow wax mold of the body part. Any problem in extracting the body part form the mold indicates that the wax mold has started to harden and it may be necessary to reinsert at least the end portion of the coated body part again into the hot wax and water container momentarily for softening thereof. The hollow wax mold is permitted to cool at room temperature and at least the interior surface of the recovered hollow wax mold is coated with a casting material and permitted to cure at room temperature. The cured, cast coated, wax mold is then immersed in the water portion of container 17 or a separate container of comparable temperature water (100°-120° F.) for a period of approximately ten minutes to remove the hollow wax mold from the casting to recover an exact casting of the body part.

The step of coating the interior surface of the recovered hollow wax mold with a casting material may involve completely filling the hollow wax mold when the body part is anything other than the face. Also, when the body part is extracted from the hollow wax mold, cosmetic trimming or shaping of the open edges of the hollow wax mold may be employed. Similarly, when the surface of the recovered hollow wax mold is coated or filled with the casting material, excess casting material may be trimmed or removed from the casting before final cure.

When making the casting illustrated in FIG. 5, any object of comparable size may be placed within the hands 62,63 and taken through the process. After the hands are removed, the object will be permanently retained in the initial casting of the hands.

Any suitable paraffin type wax having a melting point in the temperature range of 100°-120° F. may be employed for practice of the present invention. When heating container 17, the quantity of water therein causes container 17 to act as a double boiler and permits melting of the otherwise unstable paraffin without incident or spattering. Any suitable casting material may be employed for coating or filling of the wax molds in the present process. These materials include, but are not limited to, plaster of paris, casting resins, and gypsum casting materials sold under the tradenames "Hydrocal", and "Hydrosone".

Suitable release agents for coating the body parts include glycerin, or glycerol, light weight cooking oils, such as the tradename product PAM, lubricating oils, conventional sewing machine oils, such as that sold under the tradename "THREE-IN-ONE", lubricating oil sold under the tradename "WD-40", and the like.

The present process may be performed within a period of twenty minutes from the initial step of immersing the body object into the ice-water slurry to obtaining the finished product. This is in contrast to several hours required for obtaining state of the art casting of body parts. Also, the paraffin wax is reclaimed after making the casting and may be used again.

The exactness or clarity obtained in casting body parts by the present invention are such that identification of an individual may be made from fingerprints taken from the casting of a human hand. Also, facial features on face castings clearly exhibit every wrinkle, scar or mole that may be on the face.

Although the invention has been described relative to specific embodiments thereof it is not so limited and there are numerous modifications and variations thereof that will be readily apparent to those skilled in the art in the light of the above teachings. It is therefore to be understood that, within the scope of the appended claims, the invention may be practiced other than as specifically described herein.

What is claimed as new and desired to be secured by Letters Patent of the United States is:

1. A process for making an exact casting of a body part comprising the steps of:
   (a) providing a first container having a quantity of ice water therein;
   (b) providing a second container having a quantity of water and a quantity of wax therein;
   (c) heating and maintaining the second container at a temperature adequate to melt and maintain the wax in a liquid state;
   (d) coating the body part to be cast with a release agent selected from the group of release agents consisting of glycerin and light oils;
   (e) immersing the coated body part into the ice water of the first container;
   (f) immediately removing the body part from the ice water of the first container and immersing the body part into the melted wax and water in the second container;
   (g) immediately removing the wax coated body part from the melted wax and water in the second container and extracting the body part from the wax layer formed thereon to recover a unitary hollow wax mold of the body part;
   (h) permitting the hollow wax mold to cool at room temperature;
   (i) coating at least the interior surface of the recovered hollow wax mold with a curable casting material;
   (j) permitting the coated casting material to cure; and,
   (k) heating the cured, cast coated, wax mold to a temperature adequate to separate the hollow wax mold from the casting to recover an exact casting of the body part.

2. The process of claim 1 wherein the ice water contained in the first container is in the form of a ice-water slush and including the steps of providing insulation for the first and second containers and positioning the containers in adjacent relationship within a housing.

3. The process of claim 2 wherein the step of heating and maintaining the second container at a temperature adequate to melt and maintain the wax in the liquid state includes the step of providing a thermostatically controlled electric heating coil within the housing for the first and second containers.

4. The process of claim 3 wherein the wax employed in the second container is a paraffin wax and the second housing is heated and maintained at a temperature sufficient to provide a temperature range of 100°–120° F. for the water and wax contained therein.

5. The process of claim 1 wherein the steps of immersing the body part in the first and second containers are repeated at least once to provide multiple layers of wax on the hollow wax mold.

6. The process of claim 1 wherein the curable casting material is selected from the group of casting materials consisting of plaster of paris, gypsum based casting materials and casting resins.

7. The process of claim 1 wherein the hollow wax mold is filled with the casting material to recover a solid casting of the body part.

* * * * *